United States Patent [19]

Oshio et al.

[11] 4,113,463
[45] Sep. 12, 1978

[54] METHOD FOR CONTROLLING THE GROWTH OF PLANTS

[75] Inventors: Hiromichi Oshio; Hiroyuki Konishi; Shiunzi Matsumura; Kikuichi Ishikawa; Eiichi Yoneyama, all of Niihama, Japan

[73] Assignee: Sumitomo Chemical Company, Limited, Osaka, Japan

[21] Appl. No.: 776,618

[22] Filed: Mar. 11, 1977

Related U.S. Application Data

[62] Division of Ser. No. 616,995, Sep. 26, 1975, Pat. No. 4,070,176.

[30] Foreign Application Priority Data

Oct. 8, 1974 [JP] Japan .................. 49-116639
Jul. 2, 1975 [JP] Japan .................. 50-82157
Jul. 30, 1975 [JP] Japan .................. 50-93578

[51] Int. Cl.² ................... A01N 9/14
[52] U.S. Cl. .................... 71/76; 71/103; 260/397.7 R; 260/465 E; 260/508; 260/509; 260/510; 260/556 AR; 260/556 B; 560/12; 560/13; 560/110; 560/250; 562/430
[58] Field of Search ................... 71/103, 76

[56] References Cited

U.S. PATENT DOCUMENTS

| 3,772,277 | 11/1973 | Beck | 71/103 |
| 3,799,760 | 3/1974 | Stephens | 71/103 |
| 3,849,110 | 11/1974 | Soper et al. | 71/103 |

FOREIGN PATENT DOCUMENTS

| 40-17,789 | 12/1965 | Japan | 71/103 |
| 1,016,024 | 1/1966 | United Kingdom | 71/103 |

*Primary Examiner*—Joseph Paul Brust
*Attorney, Agent, or Firm*—Stevens, Davis, Miller & Mosher

[57] ABSTRACT

A method for regulating the elongation of plants so as to increase their resistance to lodging by applying a plant regulating effective amount of a plant growth regulator containing as active ingredient a benzenesulfonamide compound of the formula

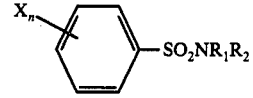

wherein X, $R_1$, $R_2$ and n are as defined hereinbelow.

15 Claims, No Drawings

METHOD FOR CONTROLLING THE GROWTH OF PLANTS

This is a Division of application Ser. No. 616,995 filed Sept. 26, 1975 now U.S. Pat. 4,070,176.

This invention relates to a method for controlling the growth of plants. More particularly, the invention is concerned with controlling the growth of plants by using a plant growth regulator containing as active ingredient a benzenesulfonamide derivative represented by the general formula,

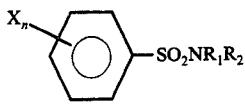

wherein X may be the same or different and is a halogen atom, an alkyl group having 1 to 5 carbon atoms, a nitro group, an amino group, an alkoxy group having 1 to 5 carbon atoms, an alkylthio group having 1 to 5 carbon atoms, an alkylsulfonyl group having 1 to 5 carbon atoms, or a group of the formula $R_3CONH-$ (where $R_3$ is an alkyl group having 1 to 5 carbon atoms); $n$ is an integer of 0 to 5; $R_1$ is hydrogen, an alkyl group having 1 to 5 carbon atoms, a phenyl group, a group of the formula —(A)—COOR$_4$ [where $R_4$ is hydrogen, an alkyl group having 1 to 5 carbon atoms, a cation such as $Na^+$, $K^+$ or $NH_4^+$ or a quaternary ammonium ion, and (A) is a group of the formula —(CH$_2$)$_m$— (where $m$ is an integer of 1 to 3), or a group of the formula

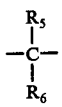

(where $R_5$ and $R_6$ are each individually hydrogen or an alkyl group having 1 to 5 carbon atoms)]; and $R_2$ is a straight chain, branched chain or alicyclic alkyl group having 1 to 15 carbon atoms, a hydroxyalkyl group having 1 to 5 carbon atoms, haloalkyl group having 1 to 5 carbon atoms, a hydroxyl group, an aminoalkyl group having 1 to 5 carbon atoms, a cyano-$C_{1-5}$-alkyl group, an alkenyl group having 2 to 5 carbon atoms, a $C_{1-5}$-alkoxy-$C_{1-5}$-alkyl group, a sulfoalkyl group having 1 to 5 carbon atoms, a phenyl-substituted alkyl group having 1 to 5 carbon atoms, or a group of the formula -(A)-COOR$_4$ [wherein $R_4$ and (A) are as defined above], when $R_1$ is hydrogen; is a hydroxyalkyl group having 1 to 5 carbon atoms, a group of the formula —(A)—COOR$_4$ wherein $R_4$ and (A) are as defined above, a group of the formula —(B)—OOCR$_7$ [where $R_7$ is a phenyl group or a alkyl group having 1 to 5 carbon atoms, and (B) is a group of the formula (CH$_2$)$_j$- (where $j$ is an integer of 1 to 3) or a group of the formula

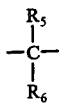

wherein $R_5$ and $R_6$ are as defined above], when $R_1$ is an alkyl group having 1 to 5 carbon atoms; and is a group of the formula —(A)—COOR$_4$, wherein $R_4$ and (A) are as defined above, when $R_1$ is a phenyl group or a group of the formula —(A)—COOR$_4$ wherein $R_4$ and (A) are as defined above.

In the cultivation of plants, the effort of controlling the growth of plants to the direction desired by human was relied over a long period of time on the improvement in variety of plants or on the technique of fertilization. As the mechanism of growth control of plants with plant hormones has been clarified in recent years, attempts of direct plant growth control using chemical substances have come to be carried out positively. As the result, there is seen such a trend that chemicals utilized actually in agriculture and horticulture are increasing in number, e.g., the utilization of α-naphthaleneacetic acid for promotion of root-taking of planted cuttings, the utilization of gibberellin for making grapes seedless, and the utilization of N-dimethylamino-succinamic acid for dwarfing of chrysanthemums. However, the fields, in which plant growth regulators have been put into practical use, are far smaller in number than the fields, in which the application of said regulators is expected. Further, even the chemicals, which have already been developed, have many such problems that they vary in effectiveness or cause phytotoxicity depending on the concentrations and the time of application thereof. Moreover, the conventional plant growth regulators vary in effectiveness, in general, depending on the kind of plant to be treated, and it is a frequently experienced fact that chemicals which have effects on broad-leaved crops are entirely ineffective for grass crops, or chemicals which have effects on wheat have no effect on rice.

With an aim to freely control the growth of various plants with chemicals, the present inventors conducted extensive studies for years to find that benzenesulfonamide derivatives have prominent plant growth-regulating actions. Based on this finding, the inventors have accomplished the present invention.

The compounds used in the present invention have such physiological characteristics that they are stronger in plant growth-controlling action than in plant growth-promoting action, and are useful in the cases where plants are required to be controlled in growth.

It is an object of this invention to provide a method for controlling the growth of plants. It is another object of this invention to provide plant growth regulating composition. It is still another object of this invention to provide a method for effectively regulating the growth of cultivated plants both in stem-leaf treatment and in soil treatment without any phytotoxicity. Other objects and advantages of this invention will be apparent from the following description.

According to this invention, there is provided a method for controlling the growth of cultivated plants by applying a plant growth regulator containing as active ingredient at least one benzenesulfonamide derivative represented by the general formula,

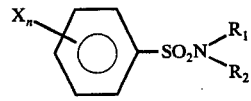

wherein X, $R_1$, $R_2$ and $n$ are the same as defined above. Preferred examples of the benzenesulfonamide derivative are the compounds wherein X can be the same or different and is a halogen atom, methyl group or methoxy group; $n$ is an integer of 0 to 3; $R_1$ is hydrogen, methyl group, ethyl group or —CH$_2$—COOH; R$_2$ is hydroxyethyl group (—CH$_2$—CH$_2$—OH), hydroxypropyl group (—CH$_2$—CH$_2$—CH$_2$—OH), hydroxybutyl group, —CH$_2$—COOH, —CH$_2$—CH$_2$—COOH, —CH(CH$_3$)—COOH, —CH$_2$—CH$_2$—CH$_2$—COOH, —C(CH$_3$)$_2$—COOH, —CH$_2$—COOCH$_3$, —CH$_2$—CH$_2$—COOCH$_3$, —CH(CH$_3$)—COOCH$_3$, when R$_1$ is hydrogen, is hydroxyethyl group, —CH$_2$—COOH, —CH$_2$—COOCH$_3$, —CH$_2$—CH$_2$—OOC.CH$_3$ or

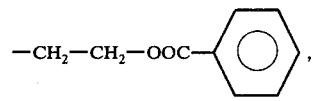

when R$_1$ is methyl or ethyl group, and is —CH$_2$—COOH, when R$_1$ is —CH$_2$—COOH. Representative benzenesulfonamide derivative which can be used in the present invention are set forth below.

| | | |
|---|---|---|
| 1) | 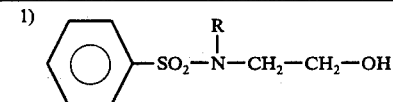 | wherein R is hydrogen, methyl or ethyl |
| 2) | 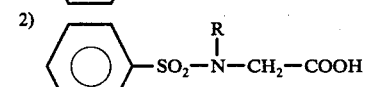 | wherein R is hydrogen, methyl or —CH$_2$COOH wherein R is —CH$_2$CH$_2$COOH, —CH$_2$CH$_2$COOCH$_3$, —CH(CH$_3$)—COOH or —CH(CH$_3$)—COOCH$_3$ |
| 3) | 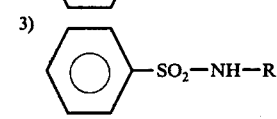 | |
| 4) | 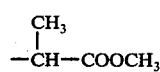 | wherein R is methyl or phenyl |
| 5) | 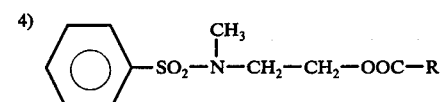 | wherein X is methyl or a halogen atom |
| 6) | 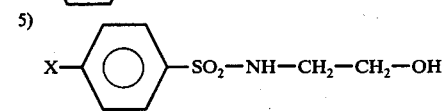 | wherein X is methoxy, chlorine or fluorine atom |
| 7) | 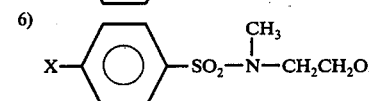 | wherein R is —CH$_2$—CH$_2$OH, —CH$_2$—CH$_2$—CH$_2$OH, —CH$_2$—CH$_2$—CH$_2$—CH$_2$—OH or —C(CH$_3$)$_2$—CH$_2$—OH |
| 8) | 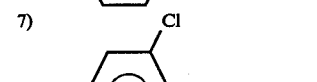 | wherein R is hydrogen or methyl |
| 9) | 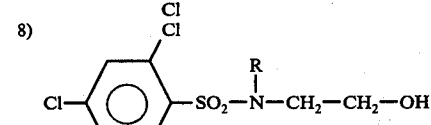 | wherein X is methyl, methoxy or chlorine and R is —CH$_2$COOH, —CH$_2$—CH$_2$COOH or —CH(CH$_3$)—COOH |
| 10) | 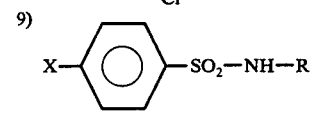 | wherein R is —CH$_2$COOH, —CH$_2$CH$_2$—COOH, —CH$_2$CH$_2$CH$_2$COOH, —CH(CH$_3$)—COOH, —CH$_2$COOCH$_3$, —CH$_2$CH$_2$COOCH$_3$, —CH$_2$CH$_2$CH$_2$COOCH$_3$ |

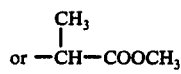
11) 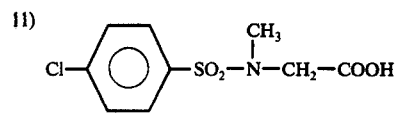
12) 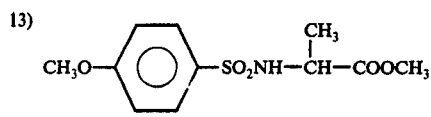
wherein R is —CH$_2$—CH$_2$—CH$_2$—COOH or —C(CH$_3$)$_2$—COOH
13) 
14) 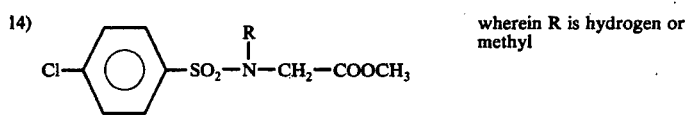
wherein R is hydrogen or methyl
15) 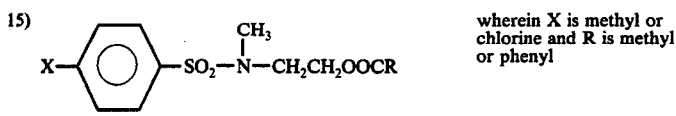
wherein X is methyl or chlorine and R is methyl or phenyl
16) 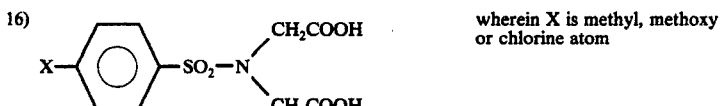
wherein X is methyl, methoxy or chlorine atom
17) 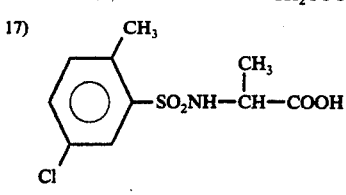
18) 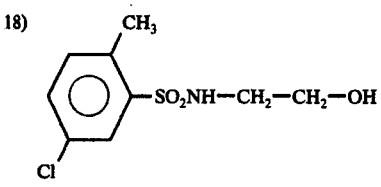
19) 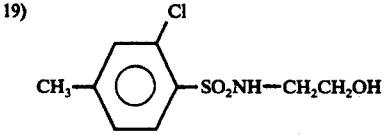
20) 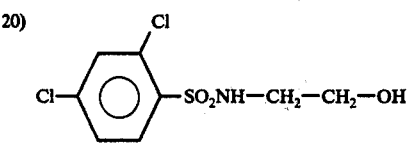
21) 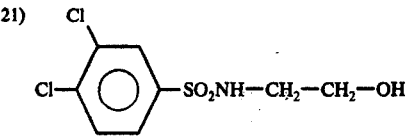
22) 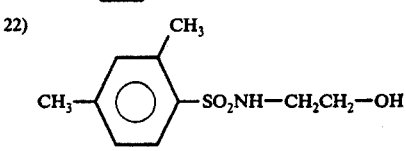

23) 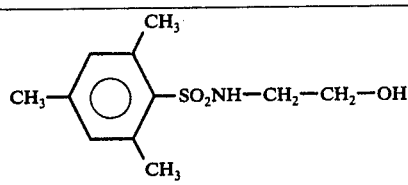

Heretofore, the aforesaid N-dimethylaminosuccinamic acid has chiefly been used as a plant growth-regulator for Pot-mum cultivation. However, it is well known that when sprayed to stems and leaves of plants, the N-dimethylamino-succinamic acid is effective, but when used in soil treatment, it is too weak in effectiveness to be used in practice. In contrast, the compounds used in the present invention show prominent growth-retarding actions both in stem-leaf treatment and in soil treatment, and hence may be said to be extremely useful plant growth regulators.

Further, the lodging of paddy rice plants and wheat plants due to typhoons and heavy rains, which are frequently encountered at the latter growth stage of said plants, lowers the ripening degree of cereal grains to invite great decrease in yield or makes the mechanical reaping of the plants difficult, and thus is a serious problem in the cultivation of said plants. While extensive studies have been made to make rice and wheat plants shorter in height by use of growth regulators so as to increase the plants in resistance to lodging, compounds which can effectively be put into practical use have not been found yet.

The compounds used in the present invention not only have actions of controlling the elongation of rice and wheat plants but also have such effects as to promote the increase in number of tillers and ears of the plants to increase the yields of rice and wheat crops. Further, they have actions of inhibiting the elongation of succulent shoot of fruit trees and turfs, and of regulating the vegetative growth of fruit trees to properly control the trees in flowering time and fruit-ripening time. Thus, the compounds of the present invention can be utilized in various fields.

Typical examples of the compounds used in the present invention and physical properties thereof are shown in Table 1 below, but compounds usable in the present invention are not limited thereto.

Table 1

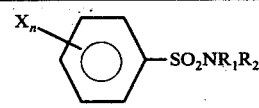

| Compound No. | $X_n$ | n | $R_1$ | $R_2$ | Physical properties |
|---|---|---|---|---|---|
| (1) | 4-CH$_3$— | 1 | —H | —C$_4$H$_9$ (n) | m.p. 36 – 38° C |
| (2) | " | " | " | " (sec) | m.p. 54 – 55° C |
| (3) | 4-Cl— | " | " | " (n) | m.p. 41.5 – 42.5° C |
| (4) | " | " | " | " (iso) | m.p. 98.5 – 99.5° C |
| (5) | " | " | " | " (sec) | m.p. 57 – 58.5° C |
| (6) | " | " | " | " (tert) | m.p. 121.5 – 122.5° C |
| (7) | " | " | " | —C$_6$H$_{13}$ (n) | m.p. 41 – 42.5° C |
| (8) | 4-CH$_3$— | " | " | —⟨phenyl⟩H | m.p. 83 – 83.5° C |
| (9) | 2,4,6-tri-Cl | 3 | " | —C$_4$H$_9$ (sec) | m.p. 106 – 107.5° C |
| (10) | " | 3 | " | —C$_{12}$H$_{25}$ (n) | m.p. 55.5 – 56° C |
| (11) | 4-CH$_3$— | 1 | " | —CH$_2$—⟨phenyl⟩ | m.p. 112– 113.5° C |
| (12) | " | " | " | —CH$_2$·CH=CH$_2$ | m.p. 60.5 – 61.5° C |
| (13) | " | " | " | —CH$_2$CH$_2$OC$_2$H$_5$ | m.p. 35.5 – 36.5° C |
| (14) | " | " | " | —CH$_2$CN | m.p. 134 – 135.5° C |
| (15) | " | " | " | —CH$_2$CH$_2$NH$_2$ | m.p. 123 – 126° C |
| (16) | 4-Cl | " | " | —CH$_2$CH$_2$CN | m.p. 84 – 86° C |
| (17) | 4-CH$_3$— | " | " | —CH$_2$CH$_2$Cl | m.p. 96.5 – 98° C |
| (18) | " | " | " | —OH | m.p. 135 – 137.5° C |
| (19) | 4-Cl— | " | " | " | m.p. 109 – 111° C |
| (20) | — | 0 | " | —CH$_2$CH$_2$OH | b.p. 194 – 197° C/2.5 mmHg |
| (21) | 4-CH$_3$— | 1 | " | " | b.p. 195° C/0.6 mmHg m.p. 50 – 51.5° C |
| (22) | 4-F— | " | " | " | m.p. 68 – 70° C |
| (23) | 4-Cl— | " | " | " | m.p. 96.5 – 98° C |
| (24) | 4-Br— | " | " | " | m.p. 82.5 – 85° C |
| (25) | 4-I— | " | " | " | m.p. 87 – 89° C |
| (26) | 2,4-di-Cl— | 2 | " | " | m.p. 68.5 – 71.5° C |
| (27) | 2-CH$_3$-4-Cl | 2 | " | " | m.p. 88 – 91° C |
| (28) | 2-CH$_3$-5-Cl— | 2 | " | " | m.p. 107 – 111° C |
| (29) | 2,4-di-CH$_3$— | 2 | " | " | m.p. 70 – 72° C |
| (30) | 2,4,6-tri-Cl— | 3 | " | " | m.p. 128.5 – 130° C |
| (31) | 4-NO$_2$— | 1 | " | " | m.p. 113 – 116° C |
| (32) | 4-CH$_3$CONH— | 1 | " | " | m.p. 121 – 123° C |
| (33) | 4-CH$_3$S— | " | " | " | m.p. 84 – 85.5° C |
| (34) | 4-CH$_3$SO$_2$— | " | " | " | m.p. 118.5 – 122.5° C |
| (35) | 4-CH$_3$O— | " | " | " | n$_D^{30}$: 1.5535 |

Table 1-continued

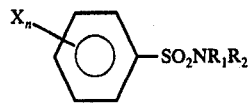

| Compound No. | $X_n$ | n | $R_1$ | $R_2$ | Physical properties |
|---|---|---|---|---|---|
| (36) | 2,4,6-tri-CH$_3$— | 3 | " | " | m.p. 74.5 – 76.5° C |
| (37) | 4-CH$_3$— | 1 | " | —CH$_2$CH$_2$CH$_2$OH | b.p. 204 – 208° C/1 mmHG |
| | | | | | m.p. 49 – 51° C |
| (38) | " | " | " | —CH$_2$CH(OH)CH$_3$ | b.p. 179 – 184° C/0.35 mmHg |
| (39) | 2,4,6-tri-Cl— | 3 | " | —CH$_2$CH$_2$OH | m.p. 104.5 – 106.5° C |
| (40) | " | " | " | —C(CH$_3$)$_2$CH$_2$OH | m.p. 128.5 – 130 ° C |
| (41) | 2,4,6-tri-CH$_3$— | " | " | " | m.p. 93.5 – 95.5° C |
| (42) | 4-Cl— | 1 | " | " | m.p. 111.5 – 114° C |
| (43) | 4-NH$_2$— | " | " | —C$_4$H$_9$ (sec) | m.p. 132.5 – 133.5° C |
| (44) | 4-Cl— | " | " | —CH$_2$CH$_2$SO$_3$H | m.p. 149 – 150° C |
| (45) | — | 0 | —CH$_3$ | —CH$_2$CH$_2$OH | b.p. 168 – 169° C/0.2 mmHg |
| (46) | 4-CH$_3$— | 1 | " | " | b.p. 184 – 186° C/0.65 mmHg |
| (47) | 4-Cl— | " | " | " | b.p. 180° C/0.5 mmHg |
| (48) | 4-F— | " | " | " | b.p. 146 – 147.5° C/0.45 mmHg |
| | | | | | m.p. 60 – 61.5° C |
| (49) | 4-CH$_3$O— | " | " | " | b.p. 198.5 – 200° C/0.85 mmHg |
| | | | | | m.p. 73.5 – 75.5° C |
| (50) | 4-NO$_2$— | " | " | " | m.p. 82.5 – 85° C |
| (51) | — | 0 | —C$_2$H$_5$ | " | m.p. 152 – 153.5° C/0.5 mmHg |
| (52) | 2-CH$_3$-5-Cl— | 2 | —CH$_3$ | " | b.p. 161 – 162° C/0.28 mmHg |
| (53) | 2,4-di-CH$_3$— | " | " | " | b.p. 164 – 165° C/0.5 mmHg |
| (54) | 2,4,6-tri-Cl— | 3 | " | " | b.p. 202 – 205° C/1.2 mmHg |
| (55) | 2,4,6-tri-CH$_3$— | 3 | " | " | b.p. 160 – 163° C/0.8 mmHg |
| (56) | — | 0 | —H | —CH$_2$COOH | m.p. 168.5 – 170° C |
| (57) | " | " | " | —CH(CH$_3$)COOH | m.p. 125.5 – 127° C |
| (58) | " | " | " | —CH(CH$_3$)COOCH$_3$ | m.p. 48.5 – 49.5° C |
| (59) | 4-CH$_3$— | 1 | " | —CH$_2$COOH | m.p. 121 – 122° C |
| (60) | " | " | " | —CH(CH$_3$)COOH | m.p. 139.5 – 140.5° C |
| (61) | " | " | " | —CH(CH$_3$)COOCH$_3$ | m.p. 57 – 59° C |
| (62) | 4-Cl— | " | " | —CH$_2$COOH | m.p. 157 – 158.5° C |
| (63) | " | " | " | —CH(CH$_3$)COOH | m.p. 142.5 – 144° C |
| (64) | " | " | " | —CH$_2$CH$_2$COOH | m.p. 134.5 – 136° C |
| (65) | " | " | " | —C(CH$_3$)$_2$COOH | m.p. 169 – 170.5° C |
| (66) | 4-CH$_3$O— | " | " | —CH$_2$COOH | m.p. 131.5 – 133.5° C |
| (67) | " | " | " | —CH(CH$_3$)COOH | m.p. 139.5 – 141° C |
| (68) | 4-CH$_3$S— | " | " | —CH$_2$COOH | m.p. 127 – 129° C |
| (69) | 4-NO$_2$— | " | " | —CH(CH$_3$)COOH | m.p. 174.5 – 175.5° C |
| (70) | 2,4-di-Cl— | " | " | " | m.p. 136.5 – 137.5° C |
| (71) | 2-CH$_3$-5-Cl— | " | " | " | m.p. 150 – 151° C |
| (72) | 2,4,6-tri-Cl— | " | " | —CH$_2$CH$_2$COOH | m.p. 164 – 165° C |
| (73) | 2,4,6-tri-CH$_3$— | " | " | —CH(CH$_3$)COOH | m.p. 155.5 – 157.5° C |
| (74) | " | " | " | —CH(CH$_3$)COOCH$_3$ | m.p. 105.5 – 107° C |
| (75) | " | " | " | —CH$_2$CH$_2$COOH | m.p. 133 – 133.5° |
| (76) | — | 0 | —CH$_3$ | —CH$_2$COOH | m.p. 183 – 184.5° C |
| (77) | " | " | " | " | m.p. 210.5 – 211.5° |

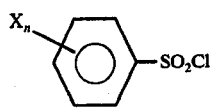

| (78) | 4-Cl— | 1 | —CH$_3$ | " | m.p. 180.5 – 182° C |
| (79) | " | " | " | —CH$_2$COOCH$_3$ | m.p. 80 – 80.5° C |
| (80) | 4-CH$_3$— | " | —CH$_2$COOH | —CH$_2$COOH | m.p. 189.5 – 190.5° C |
| (81) | 4-Cl— | " | " | " | m.p. 226° C |
| (82) | — | 0 | " | " | m.p. 194 – 195° C |
| (83) | 4-CH$_3$O— | 1 | " | " | m.p. 177 – 178.5° C |
| (84) | 2,4,6-tri-CH$_3$— | 3 | " | " | m.p. 169 – 171° C |
| (85) | 2,4-di-CH$_3$— | 2 | " | " | m.p.153 – 155° C |
| 86 | 4-CH$_3$— | 1 | —CH$_2$COOCH$_3$ | —CH$_2$COOCH$_3$ | m.p. 99 – 100° C |
| (87) | " | " | —CH$_3$ | —CH$_2$CH$_2$OOC·CH$_3$ | b.p.179 – 180° C/1 mmHg |
| | | | | | m.p. 55 – 56° C |
| (88) | 4-Cl— | " | " | " | m.p. 70– 73° C |
| (89) | — | 0 | " | " | m.p. 72 – 73° C |
| (90) | 4-CH$_3$— | 1 | " | —CH$_2$CH$_2$OOC—⬡ | m.p. 85 – 86.5° C |
| (91) | 4-Cl— | " | " | " | m.p. 50 – 50.5° C |
| (92) | — | 0 | " | " | $n_D^{22}$ 1.5632 |
| (93) | 4-CH$_3$O— | 1 | —H | —CH$_2$CH$_2$COONa | m.p. 301 –304° C |
| (94) | " | " | " | —CH$_2$CH$_2$COONH$_4$ | m.p. 142.5 – 145° C |

Generally, the compounds used in the present invention can be prepared by using the conventional methods in high yields by:

(1) reacting an aromatic sulfonyl halide of the formula (I), with a corresponding amine of the formula (II),

HNR₁R₂ (II)

in an organic solvent such as ether, dioxane, benzene, acetonitrile, tetrahydrofuran or chloroform, or a heterogeneous or homogeneous solvent system comprising said organic solvent and water, at a temperature in the range from −20° to 80° C. in the presence of a condensing agent such as amine, sodium carbonate or sodium hydroxide;

(2) reacting a carboxylic acid of the formula (III),

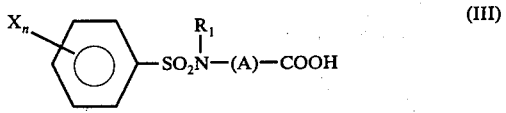

with a usual esterifying agent;

(3) reacting a carboxylic acid of the formula (III) with an alkali; or (4) reacting an alcohol of the formula (IV),

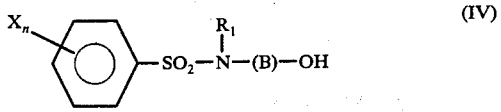

with a carboxylic acid, carboxylic acid anhydride or a carboxylic acid halide in a suitable solvent under the conventionally known conditions.

Procedures for preparing the compounds according to the present invention are illustrated by the following Examples. Unless otherwise indicated, all parts, percents, ratios and the like are by weight.

EXAMPLE 1

N-2-hydroxyethyl-2,4-dimethylbenzenesulfonamide:

To 40 parts of tetrahydrofuran are added 1.5 parts of ethanolamine and 2.5 parts of triethylamine. Into this solution, 10 parts of tetrahydrofuran containing 5 parts of 2,4-dimethylbenzenesulfonyl chloride is dropped with stirring. After the dropping, the resultant mixture is stirred as it is for 30 minutes. Subsequently, the salt is removed by filtration, and the filtrate is freed from the solvent to form a solid. This solid is recrystallized from isopropyl ether to obtain 3.6 parts of N-2-hydroxyethyl-2,4-dimethylbenzenesulfonamide, m.p. 70°–72° C.

EXAMPLE 2

N-3-hydroxypropyl-2,4,6-trichlorobenzenesulfonamide:

To 40 parts of tetrahydrofuran are added 1.4 parts of 3-amino-1-propanol and 1.8 parts of triethylamine. Into this solution, 10 parts of tetrahydrofuran containing 5 parts of 2,4,6-trichlorobenzenesulfonyl chloride is dropped with stirring. After the dropping, the resultant mixture is stirred for 1 hour. After completion of the reaction, the salt is removed by filtration, and the filtrate is freed from the solvent. The resulting oily substance is charged with water and then allowed to stand to form a solid. This solid is recrystallized from toluene to obtain 3.8 parts of N-3-hydroxypropyl-2,4,6-trichlorobenzenesulfonamide, m.p. 104.5°–106.5° C.

EXAMPLE 3

N-methyl-N-2-hydroxyethyl-benzenesulfonamide:

To 100 parts of tetrahydrofuran are added with stirring 21.3 parts of N-methyl-ethanolamine and 28.6 parts of triethylamine. To this solution, 100 parts of tetrahydrofuran containing 50 parts of benzenesulfonyl chloride is gradually added with stirring while maintaining the temperature at below 40° C. After completion of the addition, the resulting mixture is stirred as it is for a while, and then heated for about 1 hour on a water bath at 50° C. to terminate the reaction. Then, the salt is removed by filtration, and the filtrate is freed from the tetrahydrofuran to form an oily substance. This oily substance is dissolved in a mixed solvent comprising benzene and a small amount of chloroform, and the resulting solution is washed with ammonia water, further washed with water, dried over anhydrous magnesium sulfate, treated with charcoal and then freed from the solvent to obtain 55 parts of an oily substance. The thus obtained oily substance can sufficiently be used as it is, but may, if necessary, be purified by reduced pressure distillation, b.p. 168°–169° C./0.2 mmHg.

EXAMPLE 4

N-methyl-N-2-hydroxyethyl-p-chlorobenzenesulfonamide:

To 20 parts of tetrahydrofuran is added 3.9 parts of N-methyl-ethanolamine. To this solution, 10 parts of tetrahydrofuran containing 5 parts of p-chlorobenzenesulfonyl chloride is added with stirring. After completion of the addition, the resultant mixture is stirred as it is for a while, and then heated for about 1 hour on a water bath at 50° C. to terminate the reaction. Then, the salt is removed by filtration, and the filtrate is freed from the solvent, whereby an oily substance is obtained. This oily substance is subjected to distillation under reduced pressure to obtain 4.2 parts of a distillate, b.p. 180° C./0.5 mmHg.

EXAMPLE 5

N-benzenesulfonyl-α-alanine:

5 Parts of α-alanine and 4.8 parts of sodium hydroxide are dissolved in 20 parts of water. The resulting aqueous solution is charged with 5 parts of chloroform containing 10 parts of benzenesulfonyl chloride, subjected to heterogeneous phase reaction, and then stirred at room temperature for about 6 hours. After the reaction, the aqueous layer is separated and then acidified with hydrochloric acid to precipitate crystals. The crystals are collected by filtration and recrystallized from water to obtain 9.6 parts of N-benzenesulfonyl-α-alanine, m.p. 125.5°–127° C.

EXAMPLE 6

N-benzenesulfonyl-α-alanine methyl ester:

2 Parts of N-benzenesulfonyl-α-alanine is added to a diazomethane-ethereal solution. After the generation of nitrogen has ceased, the reaction liquid is freed from the ether, incorporated with a small amount of petroleum ether, and then allowed to stand in a dry ice-methanol bath to deposit crystals. The crystals are recrystallized from a mixed solvent comprising butanol and petroleum ether to obtain 1.5 parts of N-benzenesulfonyl-α-alanine methyl ester, m.p. 48.5°–49.5° C.

EXAMPLE 7

N-2,4,6-trimethylbenzenesulfonyl-α-alanine:

4.2 Parts of α-alanine and 4 parts of sodium hydroxide are dissolved in 100 parts of water. The resulting aqueous solution is added with 30 parts of chloroform containing 10 parts of 2,4,6-trimethylbenzenesulfonyl chloride, subjected to heterogeneous phase reaction, and then stirred at room temperature for 3 hours and further at 50° C. for about 7 hours. After the reaction, the upper aqueous layer is separated and then acidified with hydrochloric acid to precipitate crystals. The crystals are collected by filtration and recrystallized from a mixed solvent comprising acetone and water to obtain 6.5 parts of N-2,4,6-trimethylbenzenesulfonyl-α-alanine, m.p. 155.5°–157.5° C.

EXAMPLE 8

N-p-methoxybenzenesulfonyl-α-alanine:

2.2 Parts of α-alanine and 2.1 parts of sodium hydroxide are dissolved in 50 parts of water. Into the resulting aqueous solution, 15 parts of tetrahydrofuran containing 5 parts of p-methoxybenzenesulfonyl chloride is dropped. The resulting mixture is suspending at first, but becomes transparent after about 30 minutes. The mixture is stirred for additional 1 hour. After completion of the reaction, the reaction liquid is freed from the tetrahydrofuran by use of an evaporator and then washed with benzene, and the aqueous layer is acidified with hydrochloric acid and then allowed to stand in ice-water to precipitate crystals. The crystals are collected by filtration and then recrystallized from a mixed solvent comprising acetone and water to obtain 3.2 parts of N-p-methoxybenzenesulfonyl-α-alaine, m.p. 139.5°–141° C.

EXAMPLE 9

N-p-chlorobenzenesulfonyl-sarcosine:

4.3 Parts of sarcosine and 4.1 parts of sodium hydroxide are dissolved in 100 parts of water. To the resulting solution, 35 parts of chloroform containing 10 parts of p-chlorobenzenesulfonyl chloride is added, and the resulting mixture is stirred at 60° C. for about 2 hours. After the reaction, the aqueous layer is separated and then acidified with hydrochloric acid to precipitate crystals. The crystals are collected by filtration and recrystallized from a mixed solvent comprising acetone and water to obtain 4.6 parts of N-p-chlorobenzenesulfonyl-sarcosine, m.p. 180.5°–182° C.

EXAMPLE 10

N-p-chlorobenzenesulfonyl-sarcosine methyl ester:

2 Parts of N-p-chlorobezenesulfonyl-sarcosine is added to a diazomethane-ethereal solution. After the generation of nitrogen has ceased, the precipitated reaction product is collected by filtration to obtain 1.2 parts of N-p-chlorobenzenesulfonyl-sarcosine methyl ester, m.p. 80°–80.5° C.

EXAMPLE 11

N-p-methoxybenzenesulfonyl-iminodiacetic acid:

3.3 Parts of iminodiacetic acid and 3.2 parts of sodium hydroxide are dissolved in 50 parts of water. Into the resulting aqueous solution, 20 parts of tetrahydrofuran containing 5 parts of p-methoxybenzenesulfonyl chloride was dropped. The resulting mixture is suspending at first, but becomes transparent when stirred at room temperature for about 1.5 hours. The mixture is further stirred at 50° C. for about 20 minutes to terminate the reaction. After completion of the reaction, the reaction liquid is freed from the tetrahydrofuran and then acidified with hydrochloric acid to precipitate crystals. The crystals are collected by filtration and then recrystallized from water to obtain 3.8 parts of N-p-methoxybenzenesulfonyl-iminodiacetic acid, m.p. 177°–178.5° C.

EXAMPLE 12

N-p-toluenesulfonyl-iminodiacetic acid dimethyl ester:

2 Parts of N-p-toluenesulfonyl-iminodiacetic acid is added to a diazomethane-ethereal solution. After generation of nitrogen has ceased, the reaction liquid haing a yellow color is allowed to stand overnight. Thereafter, the ether is evaporated to form crystals. The crystals are recrystallized from methanol to obtain 2.1 parts of N-p-toluenesulfonyl-iminodiacetic acid dimethyl ester, m.p. 99°–100° C.

EXAMPLE 13

N-benzenesulfonyl-N-phenylglycine:

7.7 Parts of N-phenylglycine and 5 parts of sodium hydroxide are dissolved in 30 parts of water. Into the resulting solution, 5 parts of chloroform containing 10 parts of benzenesulfonyl chloride is dropped with stirring. After the dropping, the resulting mixture is stirred at room temperature for 4 hours and then at 50° C. for 30 minutes. Subsequently, the aqueous layer is separated from the reaction mixture and then acidified with hydrochloric acid to form an oily substance. By rubbing on the inner wall of a flask with spatula, crystallized products are formed. The crystals are recrystallized from a mixed solvent comprising methanol and water to obtain 4.2 parts of N-benzenesulfonyl-N-phenylglycine, m.p. 166°–167° C.

EXAMPLE 14

(N-methyl-N-p-chlorobenzenesulfonyl)-2-aminoethyl acetate:

To 20 parts of anhydrous benzene are added 5 parts of N-methyl-N-2-hydroxyethyl-p-chlorobenzenesulfonamide and 2.2 parts of triethylamine. Into this solution, 2 parts of acetyl chloride is dropped with stirring. After completion of the dropping, the resulting mixture is stirred as it is for a while. Subsquently, the salt is separated by filtration and washed with tetrahydrofuran. The filtrate is concentrated by means of an evaporator and then freed from the solvent under high vacuum to form a solid. This solid is recrystallized from methanol to obtain 3.7 parts of (N-methyl-N-p-chlorobenzenesulfonyl)-2-aminoethyl acetate, m.p. 70°–73° C.

EXAMPLE 15

(N-methyl-N-p-chlorobenzenesulfonyl)-2-aminoethyl benzoate:

To 30 parts of anhydrous benzene are added 5 parts of N-methyl-N-2-hydroxyethyl-p-chlorobenzenesulfonamide and 2.3 parts of triethylamine. Into this solution, 2.5 parts of benzoyl chloride is dropped. The resulting mixture is stirred for a while and then heated at 50° C. for about 1 hour. After completion of the reaction, the salt is separated by filtration and washed with tetrahydrofuran. Subsequently, the filtrate is freed from the solvent to form an oily substance. This oily substance is allowed to stand in high vacuum and then charged with water to form a solid. The solid is recrystallized from ethanol to obtain 5.2 parts of (N-methyl-N-p-chlorobenzenesulfonyl)-2-aminoethyl benzoate, m.p. 50°–50.5° C.

The benzenesulfonamide derivatives according to the present invention have prominent plant growth-regulating actions, and particularly have strong effects of controlling the elongation of heights and nodes of plants. In actual application, they may be sprayed as they are or may be used after formulating them into any of granules, dusts, emulsifiable concentrates, wettable powders and aqueous preparations.

The amount of the benzenesulfonamide derivative used varies depending on the manner of application, but when desired to be applied to soil, the benzenesulfonamide derivative is used at a concentration in the range from 0.5 to 500 p.p.m., preferably from 10 to 100 p.p.m., per part of soil, while when desired to be applied to stems and leaves by spraying, it is to use an emulsifiable concentrate or aqueous preparation containing as an active ingredient at least one benzenesulfonamide derivative at a concentration in the range from 100 to 10,000 p.p.m., preferably from 500 to 5,000 p.p.m., so that the chemical adheres to the whole stems and leaves but does not fall down as droplets. If the amount of the benzenesulfonamide derivative used is smaller than said range, the plant growth-regulating effect of the chemical is not sufficient, while if the amount thereof is larger than said range, plants are undesirably injured in growth.

Each of the preparations according to the present invention is desirably used properly according to the kind and size of cultivated plants to be treated and the purpose of application.

The granule according to the present invention is obtained by mixing the compound of the present invention as active ingredient with one or more of talc, bentonite, clay, kaolin, diatomaceous earth, vermiculite and the like extender for agricultural use, adding a fixing agent or water to the resulting mixture, sufficiently pulverizing the mixture, and then granulating the pulverized mixture.

The aqueous preparation is obtained by dissolving the present compound as active ingredient in water.

The wettable powder is obtained by adding the present compound as active ingredient and a dispersant to the aforesaid extender as carrier, and then sufficiently pulverizing the resulting mixture.

The dust is obtained by adding the present compound as active ingredient to the aforesaid extender as carrier, and then sufficiently pulverizing the resulting mixture.

The emulsifiable concentrate is obtained by adding the present compound as active ingredient to an organic solvent such as benzene, xylene, dioxane, acetone, cyclohexane, isophorone or alcohol, adding to the resulting mixture any of such emulsifiers as alkylsulfuric acid esters, alkylsulfonic acid salts, arylsulfonic acid salts, polyethylene glycol ethers, polyethylene glycol esters and polyhydric alcohol esters, and then sufficiently kneading the resulting mixture.

In actual application, the plant growth regulators of the present invention may not only be used in combination with vehicles and other surfactants used in agriculture to expect the enhancement and accuracy of the effects thereof, but may also be used in admixture with other agricultural chemicals such as fungicides, insecticides, nematocides and herbicides, and with fertilizers.

The present invention is illustrated in detail below with reference to examples, but it is needless to say that the invention is not limited to the examples, including the kinds of the compounds and additives used and the mixing proportions, but is variable within a wide scope. In the examples, the names of the compounds are represented by the exemplified numbers of the compounds.

EXAMPLE 16

500 Grams of a synthetic soil comprising sea sand, mountain soil and peat was packed in each of 12 cm unglazed pots. In each pot were cultivated three Pot-mum plants (variety: Snow Ridge). Two weeks after planting, the plants were pinched, and, 2 weeks after pinching when new buds had elongated, each of the present compounds at such concentrations as shown in Table 2 was applied to the plants. On the 42nd day after the chemical treatment, the plants were observed to investigate the plant growth-regulating effects of the present compounds. The results obtained were as set forth in Table 2.

The evaluation of the effects was carried out in such a manner that a height elongation of the plant was calculated from the difference between the initial height of the Pot-mum at the time of chemical treatment and the height thereof on the 42nd day after the chemical treatment, and was represented by a height index calculated by assuming as 100 the height of the plant of non-treated area. The value is an average value of three Pot-mum plants.

Table 2

| Compound No. | Pot-mum test Spray Treatment (4000 ppm)* | Soil Treatment (100 ppm) | Compound No. | Spray Treatment (4000 ppm)* | Soil Treatment (100 ppm) |
|---|---|---|---|---|---|
| (1) | 92 | 79 | (17) | 78 | 72 |
| (2) | 93 | 72 | (18) | 95 | 79 |
| (3) | 90 | 72 | (19) | 84 | 85 |
| (4) | 95 | 87 | (20) | 89 | 86 |
| (5) | 84 | 87 | (21) | 78 | 77 |
| (6) | 74 | 71 | (23) | 77 | 60 |
| (8) | 92 | 90 | (26) | 77 | 61 |
| (9) | 85 | 78 | (27) | 79 | 63 |
| (10) | 78 | 86 | (28) | 80 | 79 |
| (11) | 82 | 87 | (29) | 77 | 79 |
| (12) | 80 | 70 | (30) | 61 | 59 |
| (14) | 95 | 86 | (32) | 92 | 89 |
| (15) | 92 | 91 | (33) | 90 | 85 |
| (34) | 91 | 93 | (50) | 90 | 85 |
| (35) | 86 | 88 | (51) | 85 | 72 |
| (36) | 82 | 75 | (52) | 86 | 84 |
| (37) | 93 | 78 | (53) | 91 | 83 |
| (38) | 95 | 90 | (54) | 89 | 78 |
| (39) | 66 | 76 | (55) | 88 | 80 |
| (40) | 79 | 66 | (56) | 98 | 86 |
| (41) | 95 | 74 | (57) | 98 | 64 |
| (42) | 91 | 73 | (58) | 81 | 75 |
| (43) | 92 | 83 | (59) | 66 | 46 |
| (44) | 92 | 80 | (60) | 80 | 67 |
| (45) | 87 | 78 | (61) | 90 | 75 |
| (46) | 91 | 86 | (62) | 74 | 76 |
| (47) | 89 | 84 | (63) | 76 | 54 |
| (48) | 94 | 77 | (64) | 75 | 79 |
| (49) | 92 | 87 | (66) | 78 | 67 |
| (67) | 88 | 72 | (79) | 94 | 67 |
| (68) | 89 | 88 | (80) | 83 | 75 |
| (69) | 85 | 86 | (81) | 76 | 85 |
| (70) | 81 | 69 | (83) | 88 | 84 |
| (71) | 58 | 54 | (84) | 96 | 85 |
| (72) | 90 | 88 | (85) | 91 | 82 |
| (73) | 69 | 67 | (86) | 94 | 86 |
| (74) | 78 | 78 | (87) | 95 | 90 |
| (75) | 93 | 67 | N-dimethyl-amino-succinamic acid | 80 | 101 |
| (76) | 93 | 72 | | | |
| (77) | 90 | 85 | Non-treatment | 100 | 100 |

*Concentration of active ingredient

EXAMPLE 17

500 Grams of paddy soil was packed in each of plastic-made Neubauer pots. To the soil of each pot were added 25 mg. (50 p.p.m. per part of the soil) of each of the present compounds shown in Table 3 and proper amounts of fertilizer and water. Thereafter, 25 seeds of barley (variety: Yunagi) were sowed to investigate the influence of the chemical on the initial growth of the barley. The results obtained were as set forth in Table 3.

Table 3

| Compound No. | Neubauer pot test | | Compound No. | Height (Index) | Fresh weight (Index) |
|---|---|---|---|---|---|
| | Height (Index) | Fresh weight (Index) | | | |
| (3) | 91 | 98 | (24) | 54 | 69 |
| (6) | 89 | 90 | (25) | 54 | 67 |
| (7) | 90 | 91 | (27) | 85 | 97 |
| (9) | 89 | 88 | (30) | 63 | 70 |
| (11) | 93 | 97 | (31) | 89 | 98 |
| (13) | 89 | 94 | (35) | 89 | 90 |
| (14) | 85 | 80 | (42) | 76 | 78 |
| (16) | 86 | 93 | (43) | 88 | 86 |
| (17) | 85 | 89 | (45) | 52 | 57 |
| (20) | 76 | 78 | (46) | 86 | 87 |
| (21) | 90 | 92 | (47) | 67 | 70 |
| (22) | 51 | 61 | (48) | 66 | 66 |
| (23) | 76 | 88 | (49) | 69 | 75 |
| (51) | 68 | 66 | (70) | 90 | 92 |
| (52) | 82 | 89 | (72) | 81 | 85 |
| (54) | 77 | 71 | (73) | 91 | 87 |
| (56) | 67 | 73 | (75) | 91 | 107 |
| (57) | 67 | 73 | (76) | 61 | 68 |
| (58) | 66 | 82 | (77) | 79 | 81 |
| (59) | 90 | 90 | (78) | 57 | 63 |
| (61) | 91 | 98 | (79) | 66 | 77 |
| (62) | 82 | 78 | (82) | 86 | 95 |
| (63) | 69 | 82 | (83) | 78 | 91 |
| (64) | 82 | 81 | (84) | 89 | 103 |
| (65) | 81 | 82 | (85) | 90 | 93 |
| (66) | 70 | 76 | (86) | 80 | 88 |
| (67) | 88 | 98 | (88) | 72 | 86 |
| (68) | 74 | 86 | (89) | 91 | 98 |
| (69) | 70 | 69 | (90) | 59 | 77 |
| (91) | 75 | 102 | | | |
| (92) | 61 | 85 | | | |
| (93) | 71 | 76 | | | |
| (94) | 72 | 78 | | | |
| Non-treatment | 100 | 100 | | | |

EXAMPLE 18

Pot tests were carried out by using wheat plants aiming at a prevention of lodging owing to an elongation control between nodes of rice plants and wheat plants and also aiming at an increased yield owing to an increase in number of tillers and ears.

3 Kilograms of paddy soil was packed in each of Wagner pot having area of 1/5000 a, a moisture of the soil was adjusted to a field condition, 0.5 g each of N, $P_2O_5$ and $K_2O$ was applied to all layers of the soil, and then 10 seeds of wheat (variety: Ushio) were sowed on December 7th. The cultivation was carried out after adjusting to 3 plants per pot by thinning on January 23rd. The plants were treated with a definite concentration of the present compounds on March 1st and April 1st to investigate their growth thereafter.

The investigated results are shown in Table 4 below.

What is claimed is:

1. A method for regulating the elongation of plants so as to increase their resistance to lodging, characterized by applying a plant regulating effective amount of a plant growth regulator containing as active ingredient a benzenesulfonamide derivative represented by the general formula,

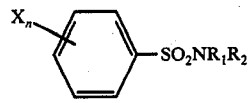

wherein X is a halogen atom, alkyl group having 1 to 5 carbon atoms, nitro group, amino group, alkoxy group having 1 to 5 carbon atoms, alkylthio group having 1 to 5 carbon atoms, alkylsulfonyl group having 1 to 5 carbon atoms, or a group of the formula $R_3CONH-$ (where $R_3$ is alkyl group having 1 to 5 carbon atoms); n is an integer of 0 to 5; $R_1$ is
  hydrogen,
  alkyl group having 1 to 5 carbon atoms,
  phenyl group, or
  a group of the formula $-(A)-COOR_4$ where $R_4$ is hydrogen, alkyl group having 1 to 5 carbon atoms, $Na^+$, $K^+$, or $NH_4^+$ ion, and
  (A) is a group of the formula $-(CH_2)_m-$ (where m is an integer of 1 to 3), or a group of the formula

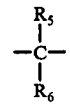

(where $R_5$ and $R_6$ are either hydrogen and alkyl group having 1 to 5 carbon atoms or are both alkyl groups having 1 to 5 carbon atoms); and $R_2$ is
  hydroxyl group, aminoalkyl group having 1 to 5 carbon atoms, cyano-$C_{1-5}$-alkyl group, a group of the formula $HSO_3-R-$ where R is an alkyl group having 1 to 5 carbon atoms, phenyl-substituted alkyl group having 1 to 5 carbon atoms, or a group of the formula $-(A)-COOR_4$ (where $R_4$ and (A) are as defined above), when $R_1$ is hydrogen; $R_2$ is
  a group of the formula $-(A)-COOR_4$ (where $R_4$ and (A) are as defined above), or a group of the formula $-(B)-OOCR_7$ where $R_7$ is phenyl group and (B) is a group of the formula $(CH_2)j-$ (where j is an integer of 1 to 3), or a group of the formula Table 4

| Compound | Date of treatment | treatment | Concentration | Plant length | | Number of stem | | Yield | |
|---|---|---|---|---|---|---|---|---|---|
| | | | | 4/18 | 5/28 | 4/18 | 5/28 | Weight of straw | Weight of unhulled wheat |
| (28) | 3/1 | Spray | 4000 ppm * | 94 | 97 | 85 | 104 | 102 | 110 |
| (30) | " | " | " | 96 | 85 | 98 | 115 | 98 | 108 |
| (28) | " | Soil | 100 mg/pot | 97 | 96 | 114 | 126 | 105 | 120 |
| (30) | " | " | " | 82 | 69 | 113 | 145 | 99 | 115 |
| (28) | 4/1 | Spray | 4000 ppm * | 90 | 98 | 86 | 101 | 101 | 108 |
| (30) | " | " | " | 86 | 97 | 102 | 110 | 91 | 107 |
| (28) | " | Soil | 100 mg/pot | 100 | 99 | 95 | 103 | 101 | 104 |
| (30) | " | " | " | 96 | 76 | 89 | 108 | 98 | 105 |
| Non-treatment | — | — | — | 100 (73 cm) | 100 (82.2 cm) | 100 (29.3) | 100 (24.3) | 100 (47.1g) | 100 (46.5g) |

* Concentration of active ingredient

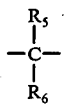

(where $R_5$ and $R_6$ are as defined above), when $R_1$ is alkyl group having 1 to 5 carbon atoms; and $R_2$ is
a group of the formula —(A)—COOR$_4$ (where $R_4$ and (A) are as defined above), when $R_1$ is phenyl group or a group of the formula —(A)—COOR$_4$ (where $R_4$ and (A) are as defined above).

2. A method according to claim 1, wherein said benzenesulfonamide derivative is applied to stems and leaves of plants by spraying with an aqueous preparation or an emulsifiable concentrate containing said compound in a concentration of 100 to 10,000 ppm.

3. A method according to claim 2, wherein said aqueous preparation or emulsifiable concentrate contains said active ingredient at a concentration of 500 to 5,000 ppm.

4. A method according to claim 1, wherein said benzenesulfonamide derivative is a compound of the formula,

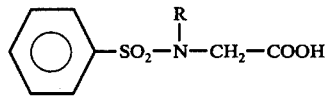

wherein R is hydrogen, methyl or —CH$_2$COOH.

5. A method according to claim 1, wherein said benzenesulfonamide derivative is a compound of the formula,

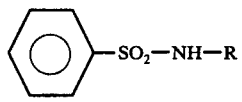

wherein R is —CH$_2$CH$_2$COOH, —CH$_2$CH$_2$COOCH$_3$,

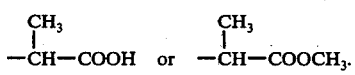

6. A method according to claim 1, wherein said benzenesulfonamide derivative is a compound of the formula,

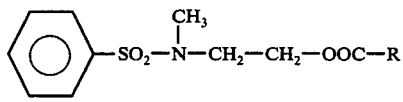

wherein R is methyl or phenyl.

7. A method according to claim 1, wherein said benzenesulfonamide derivative is a compound of the formula,

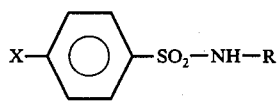

wherein X is methyl, methoxy or chlorine and R is —CH$_2$COOH, —CH$_2$—CH$_2$COOH or

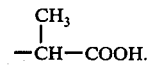

8. A method according to claim 1, wherein said benzenesulfonamide derivative is a compound of the formula,

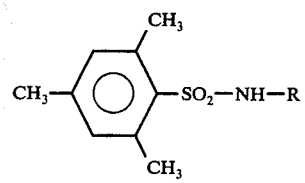

wherein R is —CH$_2$COOH, —CH$_2$—CH$_2$—COOH, —CH$_2$CH$_2$CH$_2$COOH,

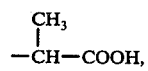

—CH$_2$COOCH$_3$, —CH$_2$CH$_2$COOCH$_3$, —CH$_2$CH$_2$CH$_2$COOCH$_3$ or

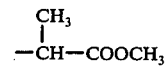

9. A method according to claim 1, wherein said benzenesulfonamide derivative is a compound of the formula,

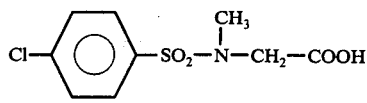

10. A method according to claim 1, wherein said benzenesulfonamide derivative is a compound of the formula,

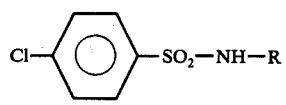

wherein R is —CH$_2$—CH$_2$—CH$_2$—COOH or —C(CH$_3$)$_2$—COOH.

11. A method according to claim 1, wherein said benzenesulfonamide derivative is a compound of the formula,

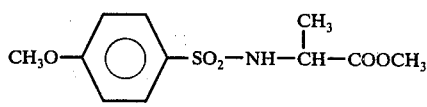

12. A method according to claim 1, wherein said benzenesulfonamide derivative is a compound of the formula,

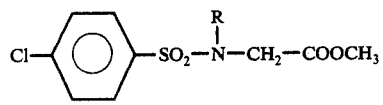

wherein R is hydrogen or methyl.

13. A method according to claim 1, wherein said benzenesulfonamide derivative is a compound of the formula,

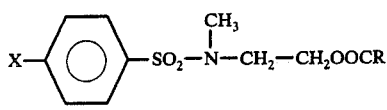

wherein X is methyl or chlorine atom and R is methyl or phenyl.

14. A method according to claim 1, wherein said benzenesulfonamide derivative is a compound of the formula,

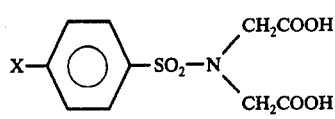

wherein X is methyl, methoxy or chlorine atom.

15. A method according to claim 1, wherein said benzenesulfonamide derivative is a compound of the formula,

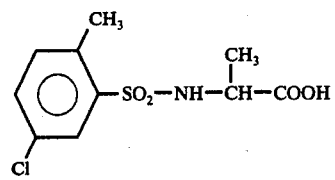

* * * * *